United States Patent
Takashima (10) Patent No.: US 7,135,610 B2
(45) Date of Patent: Nov. 14, 2006

(54) MOUSE SHOWING NEUROFIBRIL CHANGE DUE TO SENILE DEMENTIA

(75) Inventor: Akihiko Takashima, Wako (JP)

(73) Assignee: Riken, Wako (JP)

( * ) Notice: Subject to any disclaimer, the term of this patent is extended or adjusted under 35 U.S.C. 154(b) by 334 days.

(21) Appl. No.: 10/311,144

(22) PCT Filed: Jun. 14, 2001

(86) PCT No.: PCT/JP01/05070

§ 371 (c)(1),
(2), (4) Date: Dec. 13, 2002

(87) PCT Pub. No.: WO01/95709

PCT Pub. Date: Dec. 20, 2001

(65) Prior Publication Data

US 2005/0034182 A1 Feb. 10, 2005

(30) Foreign Application Priority Data

Jun. 15, 2000 (JP) ............................. 2000-179723

(51) Int. Cl.
*A01K 67/027* (2006.01)
*G01N 33/00* (2006.01)

(52) U.S. Cl. ........................................... 800/18; 800/3

(58) Field of Classification Search .................... None
See application file for complete search history.

(56) References Cited

U.S. PATENT DOCUMENTS 6,593,512 B1 * 7/2003 Vitek et al. .................... 800/18

FOREIGN PATENT DOCUMENTS

| WO | WO 99/57129 A1 | 11/1999 |
| WO | WO 99/62548 A1 | 12/1999 |
| WO | WO-01/53340 A2 | 7/2001 |

OTHER PUBLICATIONS

Brion JP, Transgenic expression of the shortest human tau affects its compartmentalization and its phosphorylation as in te pretangle stage of Alzheimer's disease, 1999, vol. 154, pp. 255-270.*

Sasahara M, PDGF B-chain in neurons of the central nervous system, posterior pituitary, and in a transgenic model, 1991, Cell, vol. 64, pp. 217-227.*

Games D, Alzheimer-type neuropathology in transgenic mice overexpressing V717F beta-amyloid precursor protein, 1995, Nature, vol. 373, pp. 523-527.*

Gotz J, Somatodendritic localization and hyperphosphorylation of tau protein in transgenic mice expressing the longest human brain tau isoform, 1995, EMBO Journal, vol. 14, pp. 1304-1313.*

Ishihara T, Age-dependent emergence and progression of a tauopathy in transgenic mice overexpressing the shortest human tau isoform, 1999, Neuron, vol. 24, pp. 751-762.*

Nacharaju P, Accelerated filament formation from tau protein with specific FTDP-17 missense mutations, 1999, FEBS Letters, vol. 447, pp. 195-199.*

Voglesbersg-Ragaglia V, Distinct FTDP-17 Missense Mutations in Tau Produce Tau aggregates and other pathological phenotypes in transfected CHO cells, 2000, Mol. Biol. Cell, vol. 11, pp. 4093-4104.*

Sahara N, Missense point mutations of Tau to segregate with FTDP-17 exhibit site-specific effects on microtubule structure in COS cells: a novel action of R406W mutation, 2000, J. Neuroscience Res., vol. 60, pp. 380-387.*

T. Frappier et al., FEBS Letters 455 (3) :262-266 (1999).

A. Takashima et al., "Characterization of transgenic mice expressing V377M human tau", Society for Neuroscience Abstracts, vol. 26, No. 1-2, Abstract No. 202.5; 30th annual meeting of the Society of Neuroscience; New Orleans, LA, Nov. 4-9, 2000, XP002298080 (abstract).

Spittaels K. et al., American Journal of Pathology, vol. 155, 1999, pp. 2153-2165.

Hasegawa M. et al., FEBS. Letters, vol. 437, 1998, pp. 201-210.

Rockenstein E. W. et al., Journal of Biological Chemistry, vol. 270, 1997, pp. 28257-28267.

C. Zehr et al., Society for Neuroscience Abstracts, vol. 25, No. 1-2 (1999), p. 1097.

Irizarry et al., The Journal of Neuroscience, Vol. 17, No. 18 (1997), pp. 7053-7059.

* cited by examiner

*Primary Examiner*—Dave Trong Nguyen
*Assistant Examiner*—David A. Montanari
(74) *Attorney, Agent, or Firm*—Birch, Stewart, Kolasch & Birch, LLP (57) ABSTRACT

A transgenic mouse transformed with a DNA encoding a mutant human tau protein, wherein the mouse exhibits neurofibrillary tangles in its brain. The transgenic mouse is useful for the development of the agent for treating neurodegenerative disorders such as Alzheimer's disease.

10 Claims, 2 Drawing Sheets

SEQUENCE LISTING

```
<160> NUMBER OF SEQ ID NOS: 9

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: myc epitope
      tag

<400> SEQUENCE: 1

Glu Gln Lys Leu Ile Ser Glu Glu Asp Leu
 1               5                  10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: FLAG
      epitope tag

<400> SEQUENCE: 2

Asp Tyr Lys Asp Asp Asp Asp Lys
 1               5

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: primer for
      PCR

<400> SEQUENCE: 3
ctgatctccg aggaggacct gatggctgag ccccgccagg ag                    42

<210> SEQ ID NO 4
```

```
<211> LENGTH: 27
<212> TYPE: DNA
<213> ORGANISM: Artificial Sequence
<220> FEATURE:
<223> OTHER INFORMATION: Description of Artificial Sequence: primer for
      PCR

<400> SEQUENCE: 4 agatttact tccatctggc cacctcc                                           27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: primer for
      PCR

<400> SEQUENCE: 5
ggaggtggcc agatggaagt aaaatca                                          27

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: primer for
      PCR

<400> SEQUENCE: 6
atcgtccttg tagtccaaac cctgcttggc caggga                                36

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: primer for
      PCR

<400> SEQUENCE: 7
cccctcgagc caccatggag cagaagctga tctccgagga ggacctg                    47

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: primer for
      PCR

<400> SEQUENCE: 8
ccgcggccgc tcacttatcg tcatcgtc                                         28

<210> SEQ ID NO 9
<211> LENGTH: 441
<212> TYPE: PRT
<213> ORGANISM: Homo sapiens

<400> SEQUENCE: 9
```

Met Ala Glu Pro Arg Gln Glu Phe Glu Val Met Glu Asp His Ala Gly
 1               5                  10                  15

Gln Asp Thr Tyr Gly Leu Gly Asp Arg Lys Asp Gln Gly Gly Tyr Thr
            20                  25                  30

Met His Gln Glu Gly Asp Thr Asp Ala Gly Leu Lys Glu Ser Pro Leu
        35                  40                  45

-continued

```
Gln Thr Pro Thr Glu Asp Gly Ser Glu Pro Gly Ser Glu Thr Ser
     50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Ala Gly Ile Gly Asp Thr Pro
                100                 105                 110

Ser Leu Glu Asp Glu Ala Ala Gly His Val Thr Gln Ala Arg Met Val
                115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
                275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
    435                 440
```

MOUSE SHOWING NEUROFIBRIL CHANGE DUE TO SENILE DEMENTIA

This application is a 371 of PCT/JP01/05070 filed Jun. 14, 2001, which claims priority from JAPAN 2000-179723 filed Jun. 15, 2000.

TECHNICAL FIELD

The present invention relates to a transgenic mouse that exhibits neurofibrillary tangles in its brain.

BACKGROUND ART

Alzheimer's disease is specific to human beings. It takes 10 years or more before its onset so that development of human disease model animals is desired in order to elucidate the cause of its occurrence or treat it. Alzheimer's disease (also called "Alzheimer type senile dementia") is macroscopically characterized by atrophy of the brain, in particular, atrophy of temporal lobe while under microscope, it shows pathological changes characteristic mainly of neurofibrillary tangles and senile plaques. Neurofibrillary tangles (NFT) are neuronal inclusions composed mainly of phosphorylated tau protein. Neurofibrillary tangles are observed in sites where neurons are abolished, besides in Alzheimer's disease, in neurodegenerative disorders with dementia (frontotemporal type dementia Parkinsonism-17 (FTDP-17) (Poorkaj, P. et al. Tau is a candidate gene for chromosome 17 frontotemporal dementia. Ann. Neurol. 43, 815–825 (1998)), Down's syndrome and several other neurodegenerative disorders). From this it is said that formation of neurofibrillary tangles is a common cascade in all the disorders that involve neurodegeneration. In other words, the formation of neurofibrillary tangles represents a final common pathway that leads to abolition of neurons in Alzheimer's disease and other neurodegenerative disorders with dementia (Spillantini, M. G. & Goedert, M. Tau protein pathology in neurodegenerative diseases. Trends Neurosci 21, 428–433 (1998)). Therefore, inhibition of neurofibrillary tangles is considered to be one of treatments for all the neurodegenerative disorders inclusive of Alzheimer's disease. However, generation of mice that cause neurofibrillary tangles has hitherto been tried using overexpression of mutant human amyloid precursor protein (Games, D. et al., Alzheimer-type neuropathology in transgenic mice overexpressing V717 β-amyloid precursor protein, Nature 373, 523–527 (1995) and Hsiao, K. et al., Correlative memory deficits, Aβ elevation, and amyloid plaques in transgenic mice, Science 274, 99–102 (1996)) or human wild-type tau protein (Tau), and although senile plaques was formed or tau protein was accumulated within cells, no neurofibrillary tangle was observed in either case. That is, although animals that express an amyloid precursor protein and presenilin were generated as a model animal for Alzheimer's disease, they did not exhibit neurofibrillary tangles which represent pathological change in dementia although they exhibit senile plaques like humans.

Also, it has been tried to generate a transgenic mouse that expresses wild human type tau protein (tau) and three lines of transgenic mice have been reported. In the transgenic mice, (1) 4 repeat tau cDNA driven by Thy-i promoter (Gotz, J. et al. Somatodendritic localization and hyperphosphorylation of tau protein in transgenic mice expressing the longest human brain tau isoform. EMBO J. 14, 1304–1313 (1995), (2) 3 repeat tau cDNA driven by 3-hydroxy-3-methylglutaryl coenzyme A reductase promoter (Brion, J. P., Tremp, G. & Octave, J. N. Transgenic expression of the shortest human tau affects its compartmentalization and its phosphorylation as in the pretangle stage of Alzheimer's disease. Am. J. Pathol. 154, 255–270 (1999)), (3) 3 repeat tau cDNA driven by prion protein promoter (Ishihara, T. et al., Age-dependent emergence and progression of a taupathy in transgenic mice overexpressing the shortest human tau isoform. Neurone 24, 751–762 (1999)) have been respectively used as a transgene.

It has been reported that among the three lines, the neurons in the lines (1) and (2) expressed approximately a 2-fold increase in tau and exhibited pretangle neuropathology while the neurons in the line (3) expressed a 5 to 10-fold increase in tau and the tau inclusions were observed in the neurons. However, none of the lines exhibited tau aggregations that showed birefringency after Congo red staining or thioflavin-S reactivity and did show formation of filamentous tau aggregations, i.e., neurofibrillary tangles.

On the other hand, there has been a report that in the mutant tau protein observed in FTDP-17, valine, which is amino acid at residue 337 is substituted with methionine (V337M) (Poorkaj, P. et al., Tau is a candidate gene for chromosome 17 frontotemporal dementia. Ann. Neurol. 43, 815–825 (1998)).

However, no report has been made on the generation of a transgenic mouse that expresses mutant human tau.

DISCLOSURE OF THE INVENTION

Thus, since the formation of neurofibrillary tangles is a common cascade for neurodegenerative disorders, the formation of neurofibrillary tangles is a useful index for the development of future pharmaceuticals for intended to treat various neurodegenerative disorders and inhibition of the formation of neurofibrillary tangles has a potential of directly leading to the therapy of neurodegenerative disorders. Therefore, a transgenic mouse exhibiting neurofibrillary tangles may provide an ideal preclinical model for the testing of therapeutic drugs for the treatment of neurodegenerative disorders such as Alzheimer's disease. Accordingly an object of the present invention is to provide a transgenic mouse useful for the development of such a therapeutic drug.

To solve the above-mentioned problem, the present inventors have made intensive investigation and, as a result, they have been found that a mouse exhibiting the same neurofibrillary tangles as observed in a human brain with Alzheimer's disease can be generated by expression of a mutant tau protein which is a cause of familial frontotemporal type dementia, and, based on the findings, they have completed the present invention.

Accordingly, the present invention provides a transgenic mouse transformed with a DNA encoding a mutant human tau protein, wherein the mouse exhibits neurofibrillary tangles in its brain.

The mutant human tau protein is preferably a mutant tau protein in which valine at a position corresponding to residue 337 in SEQ ID NO: 9 is substituted with an amino acid other than valine. The amino acid other than valine is preferably methionine.

Preferably, the transgenic mouse of the present invention is used as a model of neurodegenerative disorder.

The transgenic mouse of the present invention is preferably one characterized in that the neurofibrillary tangles are positive in immunoreactions using an antibody against a phosphorylated tau protein, an antibody against ubiquitin and an antibody against paired-helical filaments, and birefringency is shown after staining with Congo red.

Further, the transgenic mouse of the present invention preferably shows abnormal behavior.

The transgenic mouse of the present invention is preferably one in which mutant human tau protein is expressed under control of platelet growth factor β chain promoter.

The present invention also provides a method for screening for an agent for treating a neurodegenerative disorder, comprising administering a candidate substance to the above-mentioned transgenic mouse exhibiting neurofibrillary tangles, or contacting a candidate substance with a tissue or a cell from brain of the transgenic mouse, and determining an effect of the candidate substance on a property associated with the neurodegenerative disorder in the transgenic mouse or the tissue or the cell thereof, as well as, a method for producing an agent for treating aneurodegenerative disorder, comprising selecting a candidate substance by the screening method, and preparing a pharmaceutical composition comprising the selected substance.

The transgenic mouse exhibiting neurofibrillary tangles of the present invention may play an important role in elucidating the cause of neurofibrillary tangles and be useful for the development of the agent for treating all the neurodegenerative disorders exhibiting neurofibrillary tangles including Alzheimer's disease.

The transgenic mouse of the present invention, which exhibits neurofibrillary tangles, can be used as an ideal preclinic model of a neurodegenerative disorder such as Alzheimer's disease and contributes to elucidation of human neurodegenerative disorders and development of therapeutic agents therefore.

BEST MODE FOR CARRYING OUT THE INVENTION

<1> DNA Encoding Mutant Human Tau Protein

Human tau protein is known to include several isoforms. The nucleotide sequence of MRNA encoding one of isoforms of the human tau protein is registered under GenBank/EMBL/DDBJ accession No. J03778. Because the human tau protein includes isoforms, the position of amino acid is herein indicated by the number of the corresponding position in the amino acid sequence shown in SEQ ID NO: 9.

The DNA encoding mutant human tau protein used in the present invention encodes mutant human tau protein having mutation by which a mouse transformed with the DNA exhibits neurofibrillary tangles in its brain. The mutant human tau protein is preferably one observed in the disease exhibiting neurofibrillary tangles.

The mutant human tau protein having such a mutation includes one having an amino acid sequence in which the amino acid residue at 337, which is valine in the tau protein of normal person, is substituted with an amino acid other than valine (preferably methionine) and one having an amino acid sequence in which the amino acid residue at 406, which is arginine in the tau protein of normal person, is substituted with an amino acid other than arginine (preferably tryptophan).

Since it has been known that some amino acids have similar properties to those of others and that generally the amino acid sequence of a protein may contain a part that has no influence on the activity of the protein, it is expected that mutant tau protein may have mutation that has no influence on the activity that results in the neurofibrillary tangles in addition to the mutation exhibiting neurofibrillary tangles in the brain of a mouse transformed with a DNA encoding the mutant tau protein. The DNA encoding an amino acid sequence may include different nucleotide sequences due to degeneration of genetic codons.

Therefore, the nucleotide sequence of DNA encoding, for example, the mutant tau protein in which valine at 337 is substituted with methionine (hereinafter, also referred to as "V337M human tau") may have polymorphism such as substitution, deletion, or insertion of one or more nucleotides as long as V337M human tau is expressed and the transgenic mouse exhibits neurofibrillary tangles.

<2> Transgenic Mouse Exhibiting Neurofibrillary Tangles of the Present Invention The transgenic mouse of the present invention is characterized by exhibiting neurofibrillary tangles similar to those observed in the human brain with Alzheimer's disease. The neurofibrillary tangles (tau aggregation) in the brain of transgenic mouse are those satisfying pathological changes and histological characteristics characteristically observed in the brain of patients with Alzheimer's disease. Human neurofibrillary tangles refer to argento-philic nerve structures accumulated in neurons and are composed of a large number of fibrils running parallel to each other. A single fibril is called paired helical filaments (PHF). The PHF is a unique fibril that has constrictions at an interval of about 80 nm. Its basic backbone is composed of hyperphosphorylated tau. It revealed that this tau is ubiquitinated when subjected to processing.

The phrase "exhibits neurofibrillary tangles" as used herein means that in microscopic observations, neurofibrillary tangles are observed in the brain of the transgenic mouse. More specifically, one or more immunoreactions using specific antibodies against phosphorylated tau, ubiquitin and PHF, respectively, are positive or birefringency is shown after Congo red staining as in human neurofibrillary tangles. Preferably, the phrase means that all the immunoreactions using respective specific antibodies against the phosphorylated tau, ubiquitin and PHF are positive and birefringency is shown after Congo red staining.

Further, the transgenic mouse of the present invention preferably is characterized in that it shows an abnormal behavior such as antianxiety. The abnormal behavior means abnormality compared with a control animal. For example, the transgenic mouse stays on an open arm in an elevated maze for a significantly longer time than a control animal (usually, mice are apt to dislike approaching an open arm). Usually, the control animal in the maze acclimates within 2 minutes to cause a reduction in the amount of behavior. However, the transgenic mouse does not cause this.

Furthermore, human neurofibrillary tangles are present as bound with RNA and form a β-sheet structure and hence it is preferable that the β-sheet structure be observed in the neurons in the brain of the transgenic mouse by thioflavin staining, and it is also preferable that the neurofibrillary tangles be in a state where they are bound with RNA.

Specific examples of the antibodies for use in immunoreactions using specific antibodies against phosphorylated tau, ubiquitin and PHF, respectively, include PS199 as a phosphorylation dependent anti-tau antibody (Michel, G. et al., Characterisation of tau phosphorylation in glycogen synthase kinase-3β and cyclin dependent kinase-5 activator (p23) transfected cells. Biochimica et Biophysica Acta 1380, 177–182 (1998)), AT8 (Biernat, J. et al. The switch of tau protein to an Alzheimer-like state includes the phosphorylation of two serine-proline motifs upstream of the microtubule binding region. EMBO J. 11, 1593–1597 (1997)) and the like. The antibody that recognizes the structure of PHF includes an antibody specific for conformational epitope found in PHF, Alz50. For recognizing ubiquitin, anti-ubiquitin antibody may be used. Monoclonal antibodies to the above proteins can be prepared, for example, by the Cambell method using the above-mentioned proteins fixed with formalin (MONOCLONAL ANTIBODY TECHNOLOGY, Elstevier Science Publishers, Amsterdam, 1984) as antigen.

The methods for measuring the above-mentioned properties of neurofibrillary tangles are described in <4> below.

<3> Generation of Transgenic Mouse

The transgenic mouse of the present invention can be generated as follows.

(1) Preparation of Mutant Human Tau Protein (Mutant Human Tau) DNA Structure

The structure of human tau DNA is known as described above. Human tau DNA can be obtained by a method for synthesizing its entire sequence based on a known amino acid sequence or nucleotide sequence (GenBank/EMBL/DDBJ accession No. J03778, etc.), a method using PCR with primers synthesized based on a known amino acid sequence or nucleotide sequence, or the like method. The human tau DNA may have intron.

The mutant human tau DNA can be prepared, for example, by introducing mutation by site-specific mutagenesis (for example, PCR-based site-specific mutagenesis) to a known human tau DNA.

When the mutant human tau is V337V human tau, specific examples of primers for the PCR include those having nucleotide sequences shown in SEQ ID NOS: 3 to 8.

The total sequence of the prepared DNA (about 1.4 kb) can be confirmed by a DNA sequencer and the like (for example, ABI PRISM 377 DNA sequencer and the like).

(2) Transgenic Mouse

The transgenic mouse having DNA encoding the mutant tau protein and exhibiting neurofibrillary tangles can be obtained by introducing the DNA into a suitable host to transform it. The host is not particularly limited and usually used mice can be used.

The transformation, that is, introduction of DNA into a mouse, can be performed by usual methods used for a mouse, for example, a microinjection method. More specifically, DNA encoding the mutant tau protein (transgene) is introduced into an ovum by a microinjection method and the injected ovum is transplanted to a foster mother, and introduction of the gene to the chromosome of mouse is confirmed using the tail DNA of the borne littermate. Thus, a transgenic mouse can be obtained. Since the amount of mutant tau may vary among mouse lines, and among mice even within the same transgenic line, it is preferable that two or more mouse lines be used in generating transgenic mice.

The transgene can be constructed by introducing a region that is necessary for expressing neurofibrillary tangles into the mutant human tau DNA.

The region necessary for expressing neurofibrillary tangles includes a promoter to be added to the 5'-terminal, a poly-A signal to be added to the 3'-terminal and the like. The region necessary for expressing neurofibrillary tangles may be added via intron. The promoter for expressing the mutant human tau DNA sequence is not particularly limited but promoters usually used when expressing genes in a mouse may be used. As such a promoter, platelet derived growth factor (PDGF)-β chain promoter is preferably used. The PDGF-β chain promoter can be obtained from a human genome library.

Figure 1:
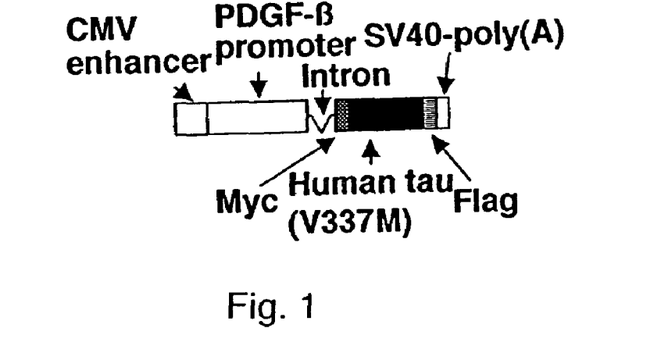
FIG. 1 shows a map of a mutant human tau-encoding construct used to generate a transgenic mouse of the present invention.

It is preferred to attach an epitope tag to the sequence of human tau protein near its N-terminal and/or C-terminal in order to distinguish the human tau protein from endogenous proteins since the human tau protein exists also as an endogenous protein, or to immunologically confirm expression of the mutant human tau. Examples of the tag epitope near the N-terminal and/or C-terminal include, for example, myc amino acid sequence (SEQ ID NO: 1) and FLAG amino acid sequence (SEQ ID NO: 2) (FIG. 1).

Whether a transgenic mouse is generated or not by microinjection can be confirmed by a genetic technique, e.g., hybridization method such as a Southern blot method using $^{32}$P-labeled human tau probe (Southern, E. M., J. Mol. Microbiol. 98, 503, 1975). Also, the expression of mutant tau protein in the transgenic mice can be immunologically confirmed by the Western blot analysis by Towbin, H. et al. (Proc. Natl. Acad. Sci. USA, 76, 4350, 1979). Further, a transgene-derived mutant tau protein can be recognized by a specific anti-tau antibody.

In the case where the transgene encodes mutant human tau labeled by epitope tags near N-terminal and/or C-terminal, the expression of tau can be confirmed by using an anti-protein antibody to the terminal tag. Also, in this case, the mutant tau protein is greater than the endogenous tau, which has a size of about 50 kD, though depending on the size of the attached epitope and the like (in Examples, the mutant tau protein is of a size of about 70 kD), so that it can be distinguished from the endogenous tau.

Specifically, whether the transformed mutant tau protein is expressed or not can be confirmed, for example, as follows. First, a transformed transgenic mouse is sacrificed, the mouse brain is homogenised in a reassembly buffer (RAB), and tau protein is recovered as heat-stable fractions, which then are separated on SDS-PAGE gel, and the separated protein is transferred on a PVDF membrane. Then using an antibody such as the above-mentioned anti-tau antibody, specific immunoreaction is performed. If the result of immunoreaction is positive, the expression of mutant tau protein is confirmed.

<4> Immunohistochemical and Histochemical Studies (1) Localization of Mutant Tau by Immunostaining The localization of mutant tau in the brain of a transgenic mouse can be determined by immunostaining with an anti-tau antibody, an antibody against a terminal tag epitope (for example, anti-myc antibody) or the like. Specifically, neurons (cerebral cortex and hippocampal region) in the brain section of a transgenic mouse are immunostained with an anti-tau antibody (for example, JM described hereinbelow), an antibody against a terminal epitope tag (for example, anti-myc antibody) or the like and the localization is confirmed under a microscope.

(2) Confirmation of Neurofibrillary Tangles by Histochemical Tests

Whether or not the transgenic mouse of the present invention exhibits neurofibrillary tangles can be confirmed as follows.

Neurons that exhibit neurofibrillary tangles (NFT) behavior generally observed in human neurodegenerative disorders such as Alzheimer's disease and frontotemporal dementia Parkinson syndrome-17 are irregularly shaped under microscopic observation and clearly distinct from other neurons. As a result, when irregularly shaped neurons or morphology resembling such neurons are observed under a light microscope or electron microscope, the existence of cells with mutant tau can be presumed.

Further, NFT are composed of a number of fibrils running parallel to each other and a single fibril is called PHF. The basic backbone of PHF is composed of hyperphosphorylated tau that is ubiquitinated and forms a β-sheet structure. As a result, when a change in which argento-philic fibrillary structure is accumulated in neurons, the neurons are presumed to show immunoreactivity for an antibody against ubiquitinated and phosphorylated tau.

Accordingly, NFT or its resembling morphology can be confirmed by performing histochemical test used for identifying NFT in human neurodegenerative disorders. The histochemical tests for detecting NFT include immunostaining a brain section from the transgenic mouse with a phosphorylation dependent anti-tau antibody (for example, PS199, AT8, etc.), an anti-ubiquitin antibody, an antibody specific for a conformational epitope of paired helical filaments (PHF) (for example, Alz50, etc.) or the like. And, whether or not a paired helical filament (PHF) epitope or the like observed in neurodegenerative disorders is formed in neurons with the mutant tau can be confirmed by measuring the above-mentioned immunoreactivity of the brain section. Further, if microscopic observation reveals the existence of linear microtubules in a portion corresponding to PHF associated with neurofibrillary tangles (NFT) in the neurons obtained from the transgenic mouse, it can be presumed that neurofibrillary tangles are formed.

(3) Confirmation of Whether or not a β-Sheet Structure is Formed by Staining

In the case of neurodegenerative disorders such as Alzheimer's disease or Parkinson syndrome, it has been known that in the neurofibrillary tangles (NFT), tau protein is phosphorylated (Morishima-Kawashima, M. et al., Proline-directed and non-proline-directed phosphorylation of PHF-tau, J. Biol. Chem., 270, 823–829 (1995), Lee, V. M., Balin, B. J., Otvos, L. Jr. & Trojanowski, J. Q. A68: A major subunit of paired helical filaments and derivatized forms of normal Tau., Science, 251, 675–678 (1991) and Woloszin, B. L., Pruchnicki, A., Dickson, D. W. & Davies, P., A neuronal antigen in the brains of Alzheimer patients, Science.232, 648–650 (1986)), and ubiquitinated (Mori, H., Kondo, J. & Ihara, Y., Ubiquitin is a component of paired helical filaments in Alzheimer's disease. Science 235, 1641–1644 (1987)) and forms a fibrillary structure of a β-sheet configuration. For this reason, whether or not a transgenic mouse exhibits neurofibrillary tangles can be also confirmed by staining with Cong red or thioflavin-S to see if a β-sheet structure is formed (upon Congo red staining, the β-sheet structure emits specific characteristic green color light under a polarizing microscope due to birefringency (Simpson, J., Yates, C. M., Watts, A. G. & Fink, G., Congo red birefringent structures in the hypothalamus in senile dementia of the Alzheimer type. Neuropathol. Appl. Neurobiol. 14, 381–193 (1988)). That is, by staining a brain section for mutant tau and then staining it with Congo red or thioflavin-S, the formation of a β-sheet structure and its localization can be confirmed. From these observations, it can be presumed that when a mutant human tau (V337M)-expressing transgenic mouse forms tau aggregations forming a β-sheet structure, it exhibits the same neurofibrillary tangles as those of human.

(4) Counterstaining with Propidium Iodide

It has been confirmed that in the neurofibrillary tangles in the brain of the Alzheimer patient, neurofibrils exist as bound to RNA (Stephen, D. et al., Sequestration of RNA in Alzheimer's disease neurofibrillary tangles and senile plaques. Ann. Neuro. 41, 200–209 (1997) and Nunomura, A. et al., RNA Oxidation is a prominent feature of vulnerable neurons in Alzheimer's disease. J. Neurosci. 19, 1959–1964 (1999)). Therefore, a transgenic mouse is preferred in which neurofibrillary tangles exist in a state where they are bound to RNA since it resembles the neurofibrillary tangles in humans.

The nucleic acids in neurons can be subjected to specific counterstaining with propidium iodide (PI). The levels of nucleic acids are proportional to the density of stain. Therefore, if a pretreatment with RNase decreases the staining of cytoplasm with PI, the existence and localization of nucleic acids can be confirmed by comparing the density before and after the pretreatment with RNase. Further, comparing the localization of mutant tau aggregations with the localization of RNA by electron microscope, the binding of RNA and tau aggregations in NFT can be confirmed.

<5> Screening and Producing Methods of Agent for Treating Neurodegenerative Disorder The transgenic mouse of the present invention can be used as a preclinic model of a neurodegenerative disorder for development of therapeutic agents for human neurodegenerative disorder.

Therefore, the present invention provides a method for screening for an agent for treating a neurodegenerative disorder by using the transgenic mouse of the present invention. The screening method of the present invention comprises administering a candidate substance to the transgenic mouse of the present invention, or contacting a candidate substance with a tissue or a cell from brain of the transgenic mouse of the present invention, and determining an effect of the candidate substance on a property associated with the neurodegenerative disorder in the transgenic mouse or the tissue or the cell thereof.

The method of administering the candidate substance to the transgenic mouse is not particularly limited, and may be a usual method used for mouse. As to the administration period, the administration is preferably performed from prior to apperance of neurofibrillary tangles to a time when neurofibrillary tangles usually appear in the transgenic mouse to which the candidate substance is not administered. The method of determining the effect of the candidate substance on the property associated with the neurodegenerative disorder in the transgenic mouse is not particularly limited either. An example thereof is a method of performing a pathological test of brain.

The tissue or the cell from brain of the transgenic mouse includes isolated tissues and cells and cultured materials therefrom. The method of contacting the candidate substance with the tissue or the cell is not particularly limited either. An example thereof is a method of determining whether tau protein insoluble even in the presence of SDS appears or not, by Western blotting.

It is preferred that the first screening is performed by contacting a candidate substance with a cell isolated from the transgenic mouse of the present invention, and then the second screening is performed by administering the candidate substance selected by the first screening to the transgenic mouse of the present invention. Specifically, the first screening is performed by simultaneously administering β-amyloid and a candidate substance to primary cultured cells of hippocampus from the transgenic mouse and determining tau protein insoluble even in the presence of SDS appears or not, by Western blotting, and the second screening is performed by administering the substance having an effect in the first screening to the transgenic mouse (for example, 10 months) and performing a pathological test to confirm an effect in the individual level.

The screening method of the present invention can be used for production of an agent for treating a neurodegenerative disorder. Namely, an agent for treating a neurodegenerative disorder can be produced by preparing a pharmaceutical composition comprising the substance selected by the screening method of the present invention. The preparation of pharmaceutical composition may be performed according to usual methods depending on kinds of the selected substance, forms of the preparation and the like.

EXAMPLE

The present invention will be described in more detail by an example. However, the present invention should not be limited thereto.

Example 1

<1> Generation of Transgenic Mice Expressing V337M Human Tau

FIG. 1 shows a map of a structure of a DNA encoding a mutant human tau used to generate a transgenic mouse of the present invention. This structure contained a cytomegalovirus (CMV) enhancer, a PDGF-β promoter, and a human tau cDNA encoding mutation of from Val to Met at the position of codon 337. Epitope tags (myc and FLAG) were attached to the N-terminal terminal and C-terminal thereof. The DNA encoding V337M human tau with myc and FLAG epitope tags was prepared by PCR-based site-specific mutation using a DNA having the nucleotide sequence of GenBank/ EMBL/DDBJ accession No. 03778 as a template. Specifically, the following three sets of PCR primers were used.

(1) Sense: SEQ ID NO: 3
  Antisense: SEQ ID NO: 4
(2) Sense: SEQ ID NO: 5
  Antisense: SEQ ID NO: 6
(3) Sense: SEQ ID NO: 7
  Antisense: SEQ ID NO: 8

The entire sequence of the cloned cDNA (1.4 kb) was confirmed by an ABI PRISM 377 DNA Sequencer. This cDNA was inserted into the XhoI and NotI sites of a PDGF-β chain expression vector prepared by inserting a cloned PDGF-β chain promoter portion into the CMV promoter portion of pCIneo vector. A 4.3 kb BglII-NaeI fragment containing PDGF-p promoter, V337M human tau cDNA and a 3'-untranslated sequence was used as a transgene to generate a mutant tau transgenic mouse (Tg) on a B6SJL background. Microinjection of the transgene and generation of transgenic mice were performed in DNX Transgenic Sciences (Cranbury, N.J., U.S.A.). As a result of the transplantation of 200 zygotes into which the transgene was introduced into foster mothers, 70 infants were obtained. Three Tg mice among them were identified by Southern blot analysis of tail DNA using $^{32}$P-labeled human tau probe. Tg mouse lines established from the three mice were named Tg216, Tg214 and Tg212, respectively.

<2> Western Blot Analysis of Tau Expression

To estimate tau expression and solubility in different buffers, brains of transgenic mice and non-transgenic littermates were carefully extracted after euthanisation with anaesthesia. Each brain was carefully parted midsagittally. The right hemisphere was used for immunohistochemistry and the left hemisphere was used for Western blot analysis. Tissue was homogenized in 400 µl of RAB (0.1 M MES, 1 mM EGTA, 0.5 mM MgSO$_4$, 0.75 M NaCl, 0.02 M NaF, and 1 mM phenylmethylsulfonyl fluoride) and centrifuged at 50,000×g for 40 minutes at 4° C. in an Optima TL ultracentrifuge (Beckman). The pellet was re-homogenized with 1 M sucrose/RAB, and centrifuged at 50,000 ×g for 20 minutes at 4° C. The resulting pellet was homogenized in 400 µl of RIPA buffer (50mM Tris, 150 mM NaCl, 1% NP40, 5 mM EDTA, 0.5% sodium deoxycholate, and 0.1% SDS, pH 8.0) and centrifuged at 100,000×g for 20 minutes at 4° C. The RIPA-insoluble pellet was solubilized in 70% formic acid (FA) and reconstituted in 50 µl Laemli SDS/ PAGE sample buffer after lyophilization. Protein concentration of each fraction was determined by Coomassie Brilliant Blue (CBB) dye (Nacalai). The samples were separated by SDS/PAGE (8% acrylamide gel). The separated protein was blotted onto Immobilon-P membrane (Millipore). After blocking the membrane with PBS containing 10% skimmed milk solution and 0.1% Tween-20, the membrane was incubated with anti-tau antibody JM diluted in PBS containing 5% skimmed milk and 0.05% Tween-20 (×10000). The membranes were developed using HRP-labeled anti-rabbit IgG polyclonal antibody. Chemiluminescent detection (ECL, Amersham) was used for visualization.

<3> Preparation of Antibodies

The following antibodies were used:

(1) Mouse monoclonal anti-myc (clone 9E10; BabCO, Calif., U.S.A.)
(2) Rabbit polyclonal anti-myc (MLC, Japan)
(3) Phosphorylation-independent rabbit polyclonal anti-tau JM (Takashima, A. et al., Presenilin 1 associates with glycogen synthase kinase-3β and its substrate tau. Proc. Natl. Acad. Sci. USA 95, 9637–9641 (1998); Jansen, Belgium)
(4) Rabbit polyclonal anti-ubiquitin (DAKO, Calif., USA)

(5) Phosphorylation-dependent rabbit monoclonal anti-tau antibody AT8 (Biernat, J. et al. The switch of tau protein to an Alzheimer-like state includes the phosphorylation of two serine-proline motifs upstream of the microtubule binding region. EMBO J. 11, 1593–1597 (1997); it recognizes the phosphorylated tau at Ser202 and Ser205; Innogenetics)

(6) Phosphorylation-dependent rabbit polyclonal anti-tau antibody PS199 (Michel, G. et al. Characterisation of tau phosphorylation in glycogen synthase kinase-3β and cyclin dependent kinase-5 activator (p23) transfected cells. Biochimica et Biophysica Acta 1380, 177–182 (1998); it recognizes phosphorylation of tau at Ser199; generously donated by Ishiguro K., Mitsubishi Kasei Institute of Life Science)

(7) Mouse monoclonal anti-tau antibody Alz50(Lee, V. M., Balin, B. J., Otvos, L. Jr. & Trojanowski, J. Q. A68: a major subunit of paired helical filaments and derivatized forms of normal Tau. Science 251, 675–678 (1991); it recognizes the conformational epitope found in paired helical filaments; generously donated by P. Davies, Einstein University).

<4> Immunohistochemical and Histochemical Studies

Brains were immersion-fixed with 10% buffered formalin, and paraffin-embedded sections (2 to 10 μm) were prepared for either light and confocal microscopic observation or electron microscopic observation (see below). Deparaffinized sections were treated in either 0.1% Triton X-100 in PBS for 20 minutes or Target Retrieval Solution (DAKO, Calif., USA). Anti-myc, JM, PS199, AT8, Alz50, and anti-ubiquitin were used as primary antibodies. Incubation in primary antibody solution occurred overnight at 4° C. Sections (2 μm) intended for light microscopic observations were incubated with mouse monoclonal anti-myc antibody as the primary antibody and goat anti-mouse IgG antibody conjugated by alkaline phosphatase as the secondary antibody. Visualization was accomplished with the HistoMark RED kit (KPL MD, USA). Sections intended for confocal laser microscopic observations were incubated with either anti-mouse Ig, labeled by Alexa488/568 (Molecular Probe), or anti-rabbit Ig, labeled by Alexa 488/568, as the secondary antibody. For nuclear counterstaining, PI or TO-PRO-3 dye (Molecular Probe) was used after treatment with RNase. PI recognizes nucleic acid. The sections were scanned with a Radiance 2000 KR3 (BIO-RAD, UK). Several sections were reacted in 0.05% Thioflavin S for 5 minutes and similarly scanned. 3 or 4 sections were stained with Congo red after confocal laser microscopic observation, and were then examined by light microscope using crossed polarizing filters (NIKON).

<5> Studies on Microtubules

After the immunohistochemical and histochemical studies, an adjacent series of paraffin-embedded sections (10 μm) were prepared for electron microscopic examination. Deparaffinized sections were hydrated and postfixed in 1% osmium tetroxide, dehydrated in various grades of ethanol, infiltrated with propylene oxide, and embedded in Araldite (trademark of TAAB). Ultrathin sections were cut with an ultramicrotome, stained with uranyl acetate and lead citrate, and examined with a JEM-1200EX transmission electron microscope at 80 kV.

<6> Evaluation Results

Evaluation results are shown below.

Figure 2:
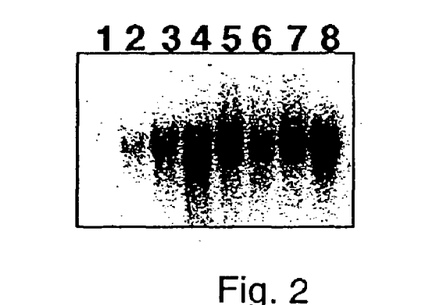
FIG. 2 shows a photograph showing the results of Southern blot analysis of a DNA fragment introduced into a transgenic mouse by using tau DNA digested with XhoI and NotI as a probe. Lane 5, Tg216; lane 6, Tg214; and lane 7, Tg212. Lane 1, null transgene copy; lane 2, 1 transgene copy; lane 3, 5 transgene copies; lane 4, 10 transgene copies; and lane 8, 20 transgene copies.

Introduction of mutant human tau DNA into mice was confirmed by Southern blot analysis. Namely, DNA fragments from Tg216 (Lane 5), Tg214 (Lane 6), and Tg212 (lane 7) line transgenic mice were analyzed by Southern blotting using XhoI- and NotI-digested tau DNA as the probe (FIG. 2). As controls, mutant human tau DNAs (Transgene) before introduction to the transgenic mice (Lanes 2 to 4 and 8) were also electrophoresed. The results revealed mutant human tau DNA was introduced in all the transgenic mice.

Figure 3:
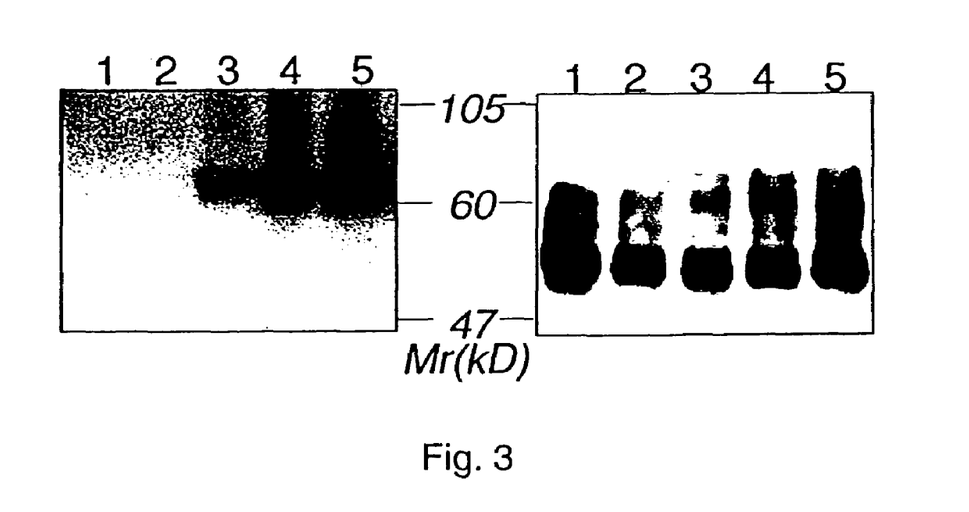
FIG. 3 shows photographs showing the results of Western blot analysis of the brain tissue of a transgenic mouse. (a) shows the results obtained by using an antibody as a probe, which is specific to the mutant human tau. Lane 1, non-transgenic littermate of Tg214; Lane 2, non-transgenic littermate of Tg216; lane 3, Tg212; lane 4, Tg214; and lane 5, Tg216. (b) shows the results obtained by using an anti-tau antibody, JM, as a probe, which recognizes both endogenous and mutant human tau. Lanes 1 to 5 are respectively given same assignments as in (a) above.

The expression of mutant human tau (V337M) in the brains of transgenic mice (Tg) was confirmed by Western blot analysis (FIG. 3(a)). Namely, RAB fraction proteins (20 μg) from the brains of mice were each supplied on 8% acrylamide gel, separated by SDS electrophoresis, and transferred to a membrane. Then, analysis was made using an anti-myc antibody, that specifically recognizes mutant human tau, as the probe and mutant human tau (V337M) was detected at the position of 70 kD. As a result, for all the transgenic mice (Lane 3, Tg212; Lane 4, Tg214; and Lane 5, Tg216), expression of mutant human tau protein was confirmed. On the other hand, in the non-transgenic mice, mutant human tau was not detected (Lane 1, nontransgenic littermate of Tg214; and Lane 2, nontransgenic littermate of Tg21).

FIG. 3(b) shows the results obtained by probing anti-tau antibody, JM, which recognizes both endogenous and mutant human tau by Western blotting. Lanes 1 to 5 are given same assignments as in FIG. 3(a). Both the transgenic and non-transgenic mice showed similar electrophoretic patterns.

Figure 4:
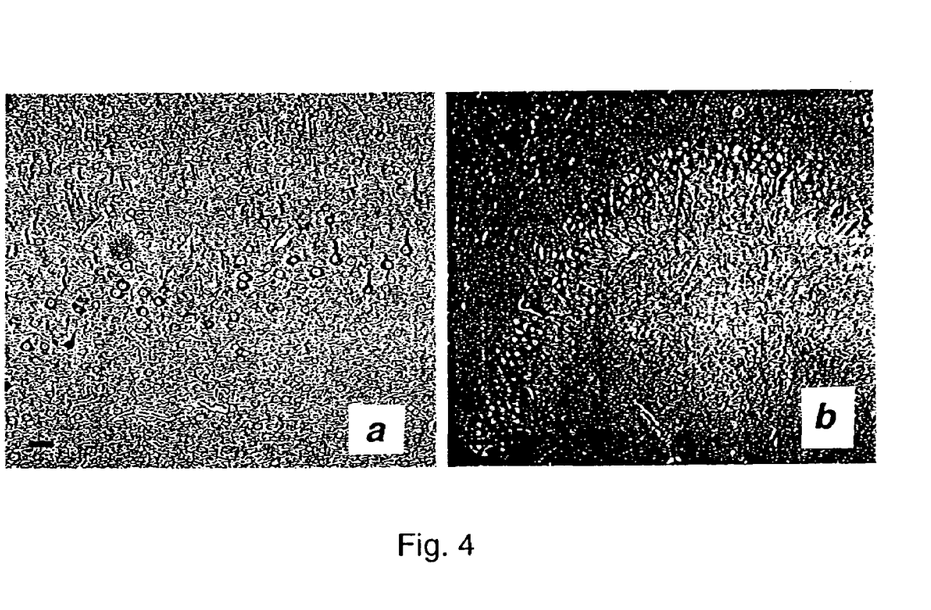
FIG. 4 shows photomicrographs showing the expression of mutant human tau. (a) shows expression in the cerebral cortex of Tg216 (Scale bar: 50 μm). (b) shows expression in hippocampus of Tg214 (scale bar: 50 μm)

Then, histological observation of brain tissues of transgenic mice was performed by staining the brain tissue sections and performing microscopic observation. Namely, Tg214 and Tg216 sections (2 μm) obtained from 10 month old mice were stained with mouse monoclonal anti-myc antibody as a primary antibody and alkaline phosphatase bound anti-mouse IgG as a secondary antibody, and then observed under light microscope. FIG. 4(a) shows the cerebral cortex of Tg216. Expression of mutant human tau in the cerebral cortex was confirmed. FIG. 4(b) shows the hippocampus of Tg214. Similarly, expression of mutant human tau in the hippocampus was confirmed (scale bar in (a) and (b); 50 μm).

As is apparent from the results shown in FIGS. 2, 3 and 4, mutant human tau DNA (V337M) was introduced into the transgenic mice (Tg212, Tg214, and Tg216) and expression of the mutant human tau DNA (V337M) in the brain tissues of the mice was confirmed.

Adjacent series of sections of hippocampal region of Tg214 (10 months old) were specifically stained with the various antibodies set forth below and histochemical characteristics of the neurons of the transgenic mice were observed. The transgenic mice tissue sections were specifically immunostained with mouse monoclonal anti-myc antibody and phosphorylation dependent rabbit polyclonal anti-tau antibody PS199. The tissue sections were also specifically immunostained with phosphorylation dependent mouse monoclonal antibody AT8 and rabbit polyclonal anti-ubiquitin antibody. Further, the sections were also specifically immunostained with rabbit polyclonal anti-myc antibody and mouse monoclonal antibody Alz50, an antibody specific to the conformational epitope found in PHF.

Figure 5:
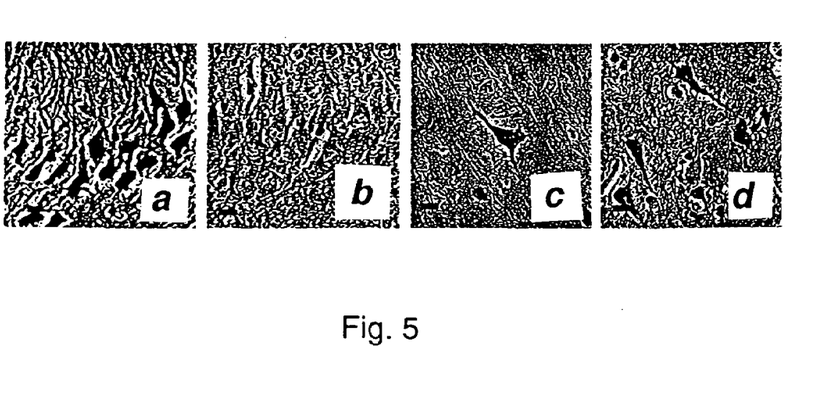
FIG. 5 shows photomicrographs of Congo red stained sections of brain tissue (scale bar: 10 μm). (a) is the hippocampus of Tg214 (10 months old). (b) is the hippocampus non-transgenic littermate of Tg214. (c) is the cerebral cortex of Tg216 (10 months old). (d) is the cerebral cortex of human brain with Alzheimer's diseases.

FIG. 5(a) to (c) are light microscopic photographs after staining mouse brain tissue sections (Tg214 (10 months old)) with Congo red. In the tissue of hippocampus of Tg214 (10 months old) (FIG. 5(a)), NFT was observed while in the littermate of Tg214, which is nontransgenic, no NFT was observed (FIG. 5(b)).

In the cerebral cortex of transgenic mice (FIG. 5(c)), NFT similar to that in the Alzheimer patient (FIG. 5(d)) was observed (scale bar: 10 μm). The existence of NFT was confirmed more significantly when observed under a polarizing microscope. Both the neurons of transgenic mice and NFT of Alzheimer patient showed clear yellow filamentous structures under a crossed polarizing filter.

From the results in FIG. 5, it is apparent that specific immunostaining of transgenic mouse brain sections and their histological analysis by microscopic observation revealed that human neurodegenerative disorders present characteristic neurofibrillary tangles.

Further, electron microscopic observation of ultrathin sections of a tissue of Tg214 mouse hippocampal neurons revealed a bundle of linear microtubules in neurons with irregularly shaped nuclear membranes. As a result of further observation at greater magnifications, the diameter of the bundle of linear fibrils was measured to be 15 to 18 nm. Thus, electron microscopic observation indicated that linear microtubules occurred at the portion corresponding to PHF associated with neurofibrillary tangles (NFT) in the neurons obtained from transgenic mice, which suggests formation of neurofibrillary tangles.

When PI staining was performed after pretreatment with RNase, PI stained only the nuclei. On the other hand, when PI staining was performed without pretreatment with RNase, both the nuclei and the locations where the neurofibrillary tangles were confirmed were stained.

In the neurofibrillary tangles occurring in human brain with Alzheimer's disease, it was confirmed that the NFT existed in a state bound to RNA. This suggests that the transgenic mice exhibit neurofibrillary tangles similar to those of humans.

Furthermore, the transgenic mouse of the present application showed abnormality in behavior such as antianxiety, which is presumed to be similar to the behavior of progressed Alzheimer patients.

Example 2

Except that R406W (arginine at 406 is substituted with tryptophan)human tau CDNA is used instead of V337M human tau cDNA, a transgenic mouse expressing R406W human tau was generated in the same way as in Example 1.

Analysis of brain sections in the same way as in Example 1<2> to <4> revealed that neurofibrillary tangles as in the V337M mouse were observed in hippocampus of the R406W mouse.

What is claimed is:

1. A transgenic mouse whose genome comprises a DNA sequence encoding a human tau protein operably linked to a promoter, wherein in said human tau protein has a mutation of valine at residue 337 of SEQ ID NO: 9 to methionine, or a mutation of arginine at residue 406 of SEQ ID NO: 9 to tryptophan, or both of said mutations, wherein the mouse brain exhibits neurofibrillary tangles.

2. The transgenic mouse according to claim 1, wherein the neurofibrillary tangles are positive in immunoreactions using an antibody against a phosphorylated tau protein, an antibody against ubiquitin and an antibody against paired-helical filaments, and birefringency is shown after staining with Congo red.

3. The transgenic mouse according to claim 1, wherein the mouse shows abnormal behavior.

4. The transgenic mouse according to claim 1, wherein the human tau protein is expressed under control of platelet-derived growth factor β chain promoter.

5. A method for screening for an agent for treating neurofibrillary tangles, comprising administering a candidate substance to the transgenic mouse of claim 1, or contacting a candidate substance with brain tissue or a neuronal cell of said transgenic mouse, and determining the effect of the candidate substance on tau phosphorylation or tangle formation.

6. The transgenic mouse according to claim 1, wherein the human tau protein is phosphorylated at serine residue 202 and 205 of SEQ ID NO: 9.

7. The transgenic mouse according to claim 1, wherein the human tau protein has the mutation of valine AT residue 337 of SEQ ID NO: 9 to methionine.

8. The transgenic mouse according to claim 1, wherein the human tau protein has the mutation of arginine at residue 406 of SEQ ID NO: 9 to tryptophan.

9. The transgenic mouse according to claim 1, wherein the human tau protein has the mutation of valine at residue 337 of SEQ ID NO: 9 to methionine and the mutation of arginine at residue 406 of SEQ ID NO: 9 to tryptophan.

10. The transgenic mouse according to claim 7, wherein the human tau protein is expressed under control of platelet-derived growth factor β chain promoter.

* * * * *